(12) United States Patent  
Thakore et al.

(10) Patent No.: US 11,660,385 B1
(45) Date of Patent: May 30, 2023

(54) PACKAGE FOR MEDICAL DEVICE

(71) Applicant: Becton, Dickinson and Company, Franklin Lakes, NJ (US)

(72) Inventors: Bhanupratapsingh Dharmendrasingh Thakore, Vadodara Gujarat (IN); Preetika Singh, Meerut (IN); Satyabhan Jat, Bangalore (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/828,705

(22) Filed: May 31, 2022

(51) Int. Cl.
*A61M 5/00* (2006.01)
*B65D 65/22* (2006.01)

(52) U.S. Cl.
CPC ............. *A61M 5/002* (2013.01); *B65D 65/22* (2013.01); *B65D 2575/3227* (2013.01)

(58) Field of Classification Search
CPC .............................. A61M 5/002; B65D 65/22; B65D 2575/3227
USPC .................................................. 206/364, 815
See application file for complete search history.

(56) References Cited

U.S. PATENT DOCUMENTS

| 4,801,073 A | 1/1989 | Farber |
| 5,409,115 A | 4/1995 | Barkhorn |
| 5,830,547 A | 11/1998 | MacKenzie et al. |
| 6,343,876 B2 | 2/2002 | Takahashi et al. |
| 6,643,995 B1 * | 11/2003 | Koyama ................ B65D 75/32 53/329.3 |
| 8,727,117 B2 | 5/2014 | Maasarani |
| 10,011,086 B2 | 7/2018 | Lahti et al. |
| 2003/0168365 A1 * | 9/2003 | Kaern ................ B65D 75/5855 206/466 |
| 2008/0061120 A1 | 3/2008 | Nowak et al. |
| 2011/0266334 A1 | 11/2011 | Keltsch |
| 2013/0066292 A1 * | 3/2013 | Ueda ..................... A61J 1/1462 604/404 |
| 2013/0295242 A1 | 11/2013 | Cheema |
| 2014/0084004 A1 * | 3/2014 | Kanderka .......... B65D 75/5827 220/276 |
| 2014/0287106 A1 | 9/2014 | Molla et al. |
| 2014/0301675 A1 | 10/2014 | Keltsch |
| 2018/0153769 A1 * | 6/2018 | Dey .................... B65D 75/327 |
| 2022/0112018 A1 * | 4/2022 | Montano ................ B65D 65/40 |

FOREIGN PATENT DOCUMENTS

| WO | 2004101387 A1 | 11/2004 |
| WO | 2016024963 A1 | 2/2016 |

\* cited by examiner

*Primary Examiner* — Jacob K Ackun
(74) *Attorney, Agent, or Firm* — Servilla Whitney LLC

(57) ABSTRACT

Packages comprising a film surrounding the medical device are described and including a tear-enabling feature and a gripping feature enabling a user to use a finger, a thumb or an end of a tool to apply a sufficient tearing force to cause the tear-enabling feature to tear and move the first end of the package away from the second end of the package using only one hand and to expose the medical device to be accessed for use. Also described are methods of packaging a medical device.

28 Claims, 13 Drawing Sheets

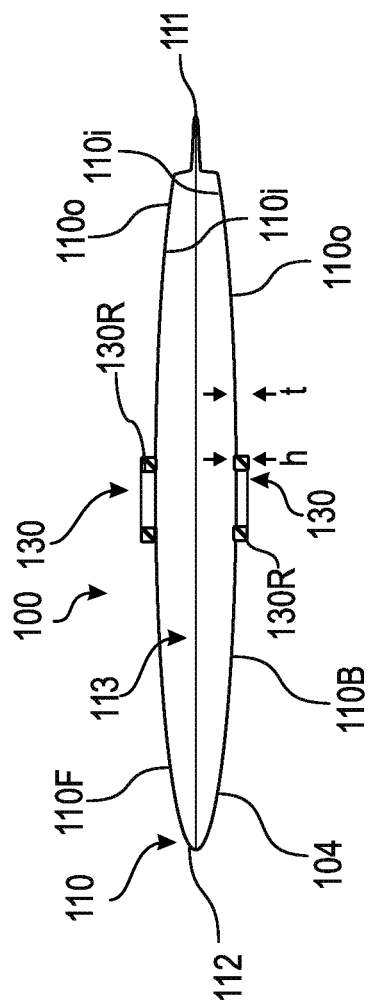
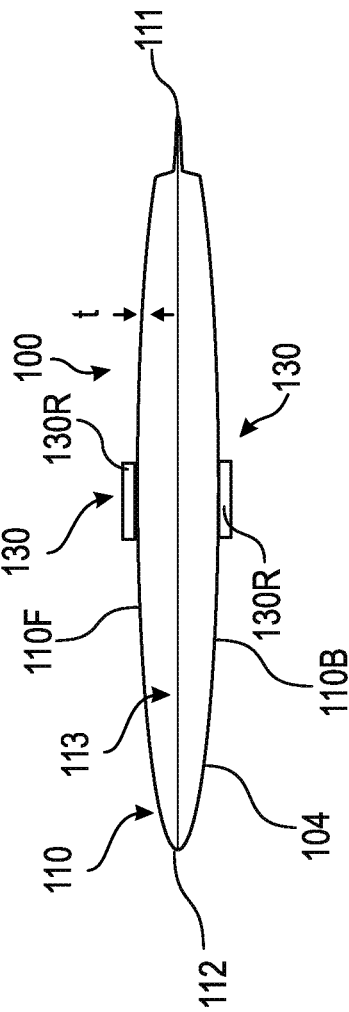
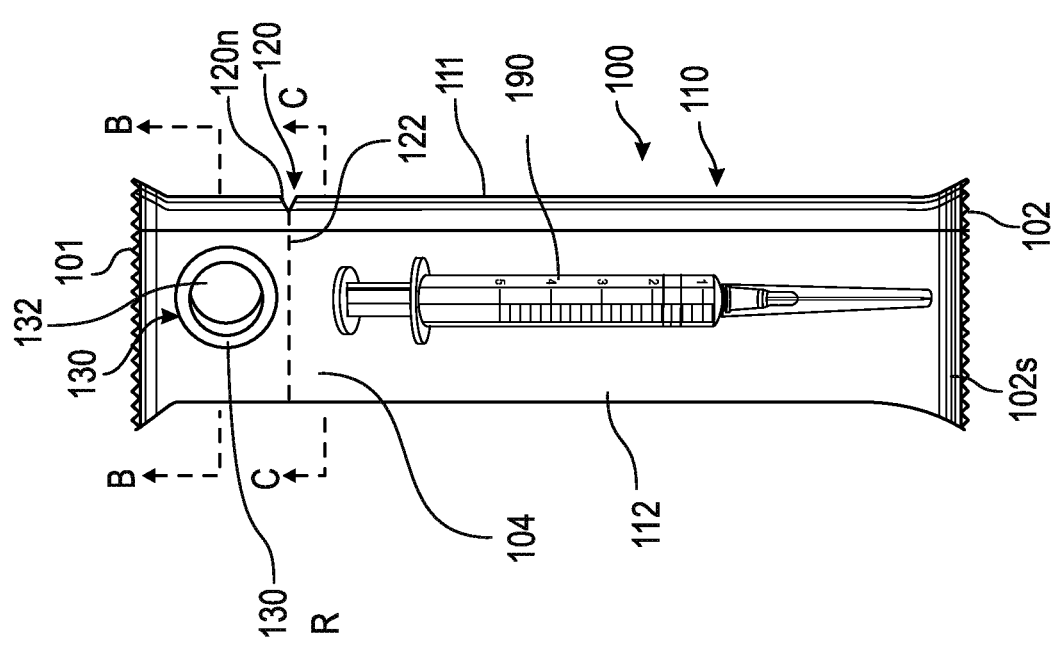
FIG. 5A
FIG. 5B
FIG. 5C

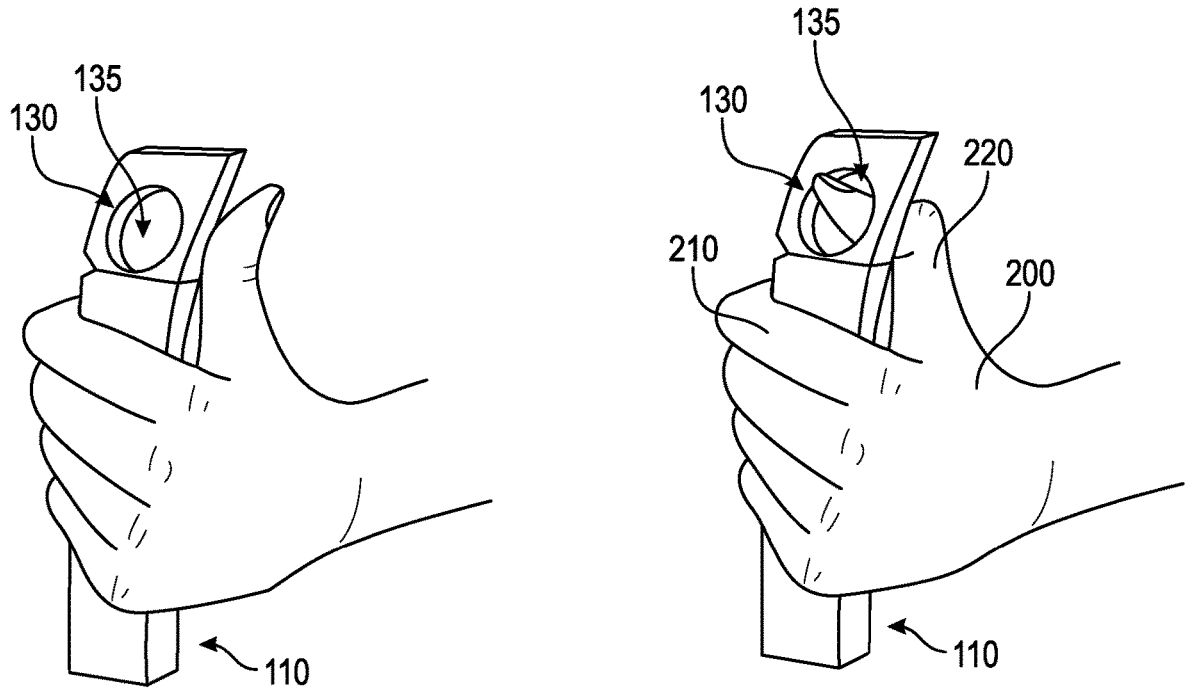
FIG. 11A
FIG. 11B
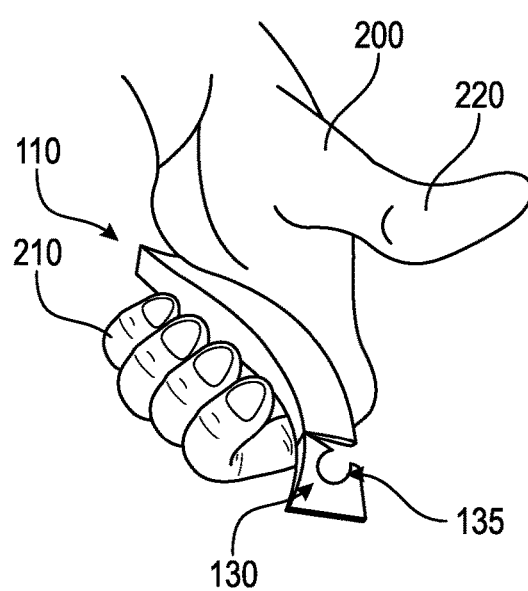
FIG. 11C

PACKAGE FOR MEDICAL DEVICE

TECHNICAL FIELD

The present disclosure relates to packages, and more particularly to a package housing a medical device, such as a syringe.

BACKGROUND

Clean or sterile articles used in medical applications are packaged to preserve their sterility. The packaging for these articles is intended to provide a barrier to prevent microorganisms from entering inside the packaging to contaminate the contents of the packaging. In most instances, the packaging is opened immediately prior to using the article, for example, a blister pack housing a syringe to minimize the time period in which the article is exposed to unsterile conditions.

Traditionally, to prevent contamination, a medical device is loosely located within conventional blister packaging. The blister packaging provides an enclosure which is sealed against entrance of contaminants and prevents contamination of the syringe. Conventional blister packaging, however, requires two hands and the knuckle-roll-peel technique to open the packaging.

In the challenging environment of a hospital, emergency care center, ambulance or other medical setting, where there is little time to fumble with syringe packaging, this two-handed opening process is cumbersome and time-consuming. Medical practitioners such as doctors, nurses, physician assistants, paramedics and emergency medical technicians are often doing multiple tasks at one time, and, because of the design of conventional blister packaging, the medical practitioner must free up both of their hands to open the blister package in order release a medical device from a package.

Additionally, the traditional two-handed knuckle-roll-peel technique required to open conventional blister packaging often compromises sterility. The packaging, if opened in the wrong direction or in haste, can tear or fracture. Such tearing introduces foreign matter into the syringe product, exposing the syringe to unsterile conditions.

Furthermore, conventional blister packaging consumes a significant amount of material as the packaging requires a peel tab for the user to open the package. This extra packaging material leads to an increase in the cost of each syringe product. Moreover, the additional packaging then needs to be discarded upon opening the package, leading to an increase in the amount of waste material produced in a hospital or other medical setting.

FIGS. 1-4 show a conventional (prior art) syringe package and opening of a conventional syringe package. FIGS. 1 and 2 illustrate a conventional syringe package. Referring to FIG. 1, the package 2 includes a syringe 4 and a blister package 6. The blister package 6 comprises a flexible web sealed to a backing thus defining a compartment and providing a sealed region 8 about the periphery of the backing for containing the syringe 4. The blister package also includes at least one peel tab 9 for the medical practitioner to use when opening the blister package to release the syringe. Referring to FIG. 2, the width of the sealed region 8 is equivalent around the entire periphery of the backing. In other words, whatever the sealing mechanism, the sealed region has the same dimension between the syringe and edge of the package around the entire package 6.

FIGS. 3 and 4 illustrate the opening of a conventional syringe package. Referring to FIGS. 3 and 4, with a knuckle-roll motion, the outer packaging material is peeled apart using two hands, and the product is released. In other words, the two-handed knuckle-roll-peel technique used to open the package 2 requires placing the knuckles of both hands on either side of the peel tabs 9 of package 2 and using the thumbs to roll and peel the seal apart, peeling the flexible web away from the backing to reveal the syringe 4 separate from the blister pack 6. This two-handed opening is very cumbersome and time-consuming for the medical practitioner, as it requires the medical practitioner to free-up both hands for opening the package. Additionally, the traditional two-handed knuckle-roll-peel technique required to open conventional blister packaging often compromises sterility. The packaging, if opened in the wrong direction or in haste, can tear or fracture. This fiber tear is the delaminating of either the top or bottom web of the blister packaging material. Such tearing introduces foreign matter into the syringe product, exposing the syringe to unsterile conditions.

It would be advantageous to provide a package to house a medical device, for example, a syringe that does not require the two-handed knuckle roll peel technique to open and that does not include a peel tab for opening.

SUMMARY

Aspects of the disclosure are directed to medical device packages and packaged medical devices. In a first aspect, a packaged medical device comprises a medical device contained in a package, and the package comprises a film surrounding the medical device, the film sealed at a first end and a second end and defining an enclosure comprising a front side, a back side, the first end and the second end, the film comprising a tear strength; a tear-enabling feature selected from at least one of a notch and a perforation at a location adjacent the first end, the tear-enabling feature reducing the tear strength of the film at the location of the tear-enabling feature; and a gripping feature formed in the film located between the first end and the tear-enabling feature, the gripping feature configured to allow a user to use a finger, a thumb or an end of a tool to apply a sufficient tearing force to cause the tear-enabling feature to tear and move the first end of the package away from the second end of the package using only one hand and to expose the medical device to be accessed for use.

A second aspect is directed to a system comprising the packaged medical device described herein such as the medical device according to the first aspect; and a hook-shaped tool configured to engage the gripping feature.

A further aspect is directed to a method of packaging a medical device, the method comprising surrounding the medical device with a film and sealing the film at a first end and a second end to define an enclosure comprising a front side, a back side, the first end and the second end, the film comprising a tear strength; including in the film a tear-enabling feature selected from at least one of a notch and a perforation at a location adjacent the first end, the tear-enabling feature reducing the tear strength of the film at the location of the tear-enabling feature; and forming a gripping feature in the film located between the first end and the tear-enabling feature, the gripping feature configured to allow a user to use a finger, a thumb or an end of a tool to apply a sufficient tearing force to cause the tear-enabling feature to tear and move the first end of the package away from the second end of the package using only one hand and to expose the medical device to be accessed for use.

BRIEF DESCRIPTION OF THE DRAWINGS

FIG. 5A is a front view of a packaged medical device according to an embodiment of the disclosure;

FIG. 5B is a cross-sectional view taken along line B-B of FIG. 5A;

FIG. 5C is a cross-sectional view taken along line C-C of FIG. 5A;

FIGS. 11A-C are front views showing use of the package and illustrating how the package can be opened according to an embodiment;

DETAILED DESCRIPTION

Figure 2:
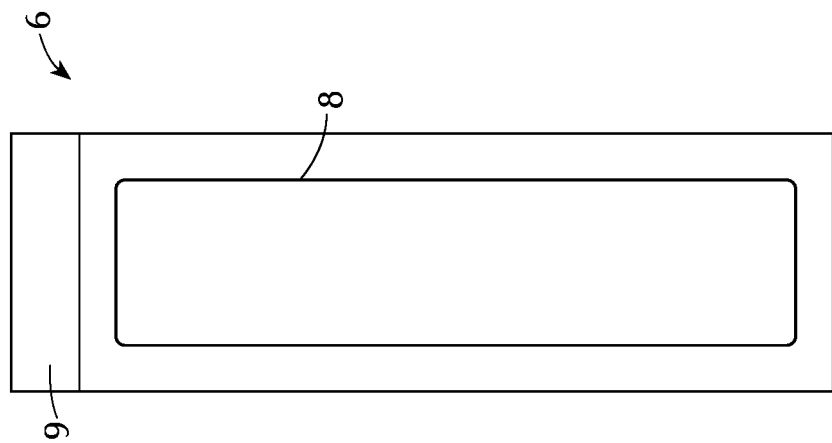
FIG. 2 is a top plan view of a prior art syringe package.
Figure 1:
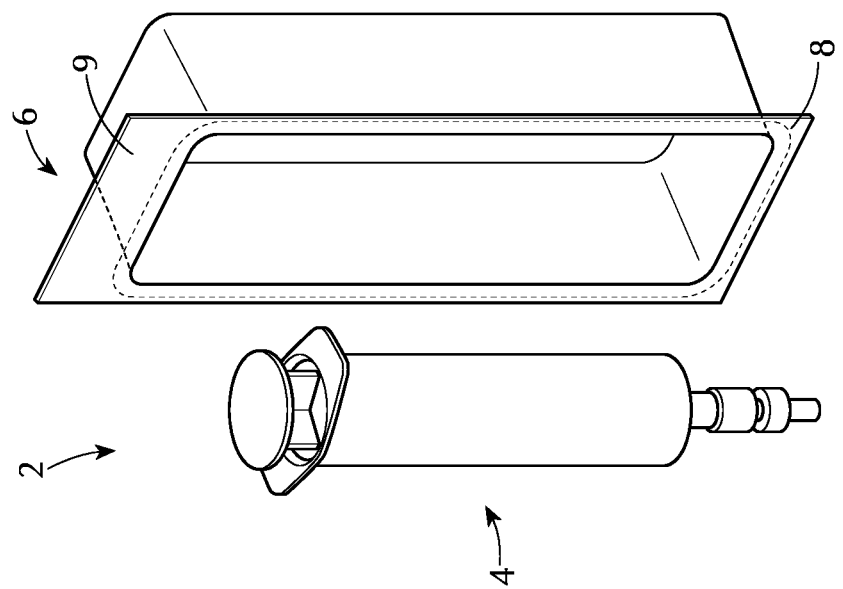
FIG. 1 is a perspective view of a prior art syringe package and a syringe adjacent to the package.
Figure 3:
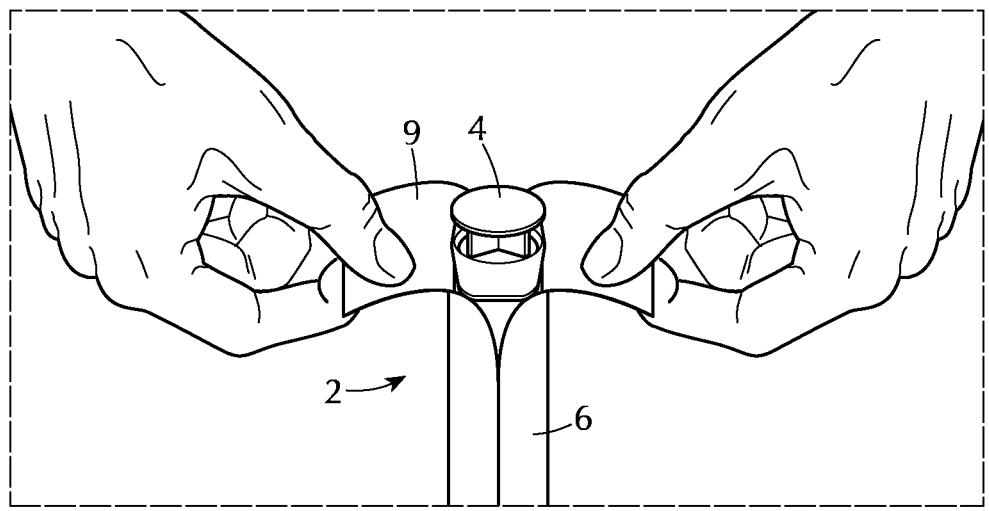
FIG. 3 is a perspective view showing a user/practitioner opening a prior art syringe package.
Figure 4:
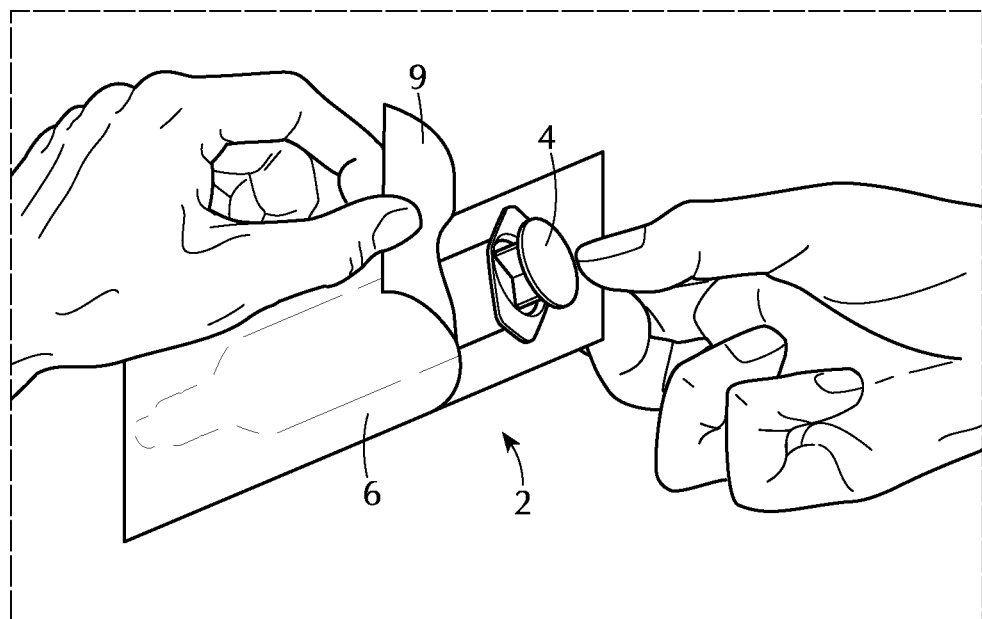
FIG. 4 is a side perspective view showing a user/practitioner opening a prior art syringe package.

Before describing several exemplary embodiments of the disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

As used herein, the use of "a," "an," and "the" includes the singular and plural.

Reference to "medical device" refers to any device intended to be used for medical purposes, for example, a syringe. Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the procedure and the medical practitioner.

As used herein, the terms "package" or "packaging" includes any material used to wrap or protect a good or product, such as a syringe. Packaging can be rigid or flexible. Packaging includes, but is not limited to, medical packaging, pharmaceutical packaging, and child-resistant packaging.

Tyvek® is a synthetic material consisting of flashspun high-density polyethylene fibers (i.e., a spunbound olefin fiber). The material is lightweight and strong and is resistant to tearing but can be cut with scissors or a knife. Water vapor and other gases can pass through Tyvek® as the material is highly breathable, but, at the same time, the material is impermeable to liquid water and microorganisms.

As used herein, the term "sterilization" refers to a means of eliminating or killing microorganisms present on a surface, contained in a fluid or in a compound such as biological culture media in order to achieve asepsis or a sterile microbial environment. Sterilization can be achieved by applying heat, chemicals, irradiation/radiation, high pressure, filtration, or combinations thereof. Chemical sterilization includes sterilization with gases such as ethylene oxide, hydrogen peroxide gas, and ozone, liquids such as chlorine bleach, iodine, glutaraldehyde and formaldehyde, ortho-phthaladehyde (OPA), hydrogen peroxide, peracetic acid, sodium hydroxide, silver, and cobalt. Radiation sterilization involves the use of radiation such as electron beams (E-beam), x-rays, gamma rays, or subatomic particles.

Embodiments of the instant disclosure pertain to packages that include a syringe surrounded by a package, incorporating features for opening the package with only one hand, while maintaining sterility of the syringe. In one or more embodiments, removal of a medical device from the package is less cumbersome than from a conventional package. In one or more embodiments, the package is a flow-wrapped package.

Referring now to FIGS. 5A-C, an embodiment of the disclosure pertains to a packaged medical device 100 comprising a medical device 190 contained in a package 110. In one or more embodiments the package 110 comprises a film 104 surrounding the medical device 190, the film 104 sealed at a first end 101 and a second end 102 and defining an enclosure 113 comprising a front side 110F, a back side 110B, the first end 101, the second end 102, a first edge 111, and a second edge, the film 104 comprising a tear strength.

The package 110 further comprises a tear-enabling feature 120 selected from at least one of a notch and a perforation 122 at a location on one of the first edge 111 and the second edge 112 and adjacent the first end 101, the tear-enabling feature 120 reducing the tear strength of the film 104 at the location of the tear-enabling feature 120. The package 110 further comprises a gripping feature formed in the film 104 located between the first end 101 and the tear-enabling feature 120, the gripping feature configured to allow a user to use a finger, a thumb or an end of a tool to apply a sufficient tearing force to cause the tear-enabling feature 120 to tear and move the first end 101 of a package 110 away from second end 102 of a package 110 using only one hand and to expose the medical device 190 to be accessed for use.

In one or more embodiments, the medical device 190 comprises a syringe as shown, and in some embodiments, the syringe 12 is sterile. In one or more embodiments, the gripping feature 130 is selected from the group consisting of a raised area 130R in the film 104 and an opening 132 through the film 104. The raised area 130R has a thickness such that the raised area 130R has a height h (shown in FIG. 5B) that is greater than a thickness t of the film 104. In one or more embodiments, the package material comprises low density polyethylene having a thickness in a range of 30 to 40 microns, and the film is wrapped around the medical device using a flow wrapping process.

In some embodiments, the height of the raised area 130R is 2 times, 3 times, 4 time, 5 times, 6 times, 7 times, 8 times, nine times, 10 times, 15 times or 20 times greater than the thickness t of the film 104. The height of the raised area 130R should provide sufficient strength to the gripping feature 130 so that when a user exerts a pulling force on the gripping feature 130, the film 104 tears at the tear-enabling feature 120 so that the first end 101 of the package 110 can be torn at the tear-enabling feature to expose the medical device 190 to be removed from the package 110. In some embodiments of the packaged medical device 100, the gripping feature comprises a raised area 130R in the film 104, the raised area 130R having a height h that is greater than a thickness t of the film 104 and providing a surface to allow the user to apply the sufficient tearing force to tear open the package 110 to allow the medical device 190 to be removed from the package 110.

Figure 8A:
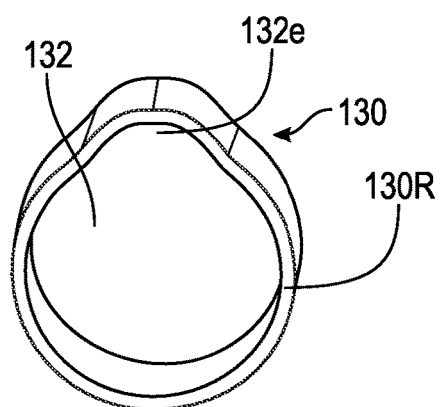
FIGS. 8A-E show alternate embodiments of opening shapes.
Figure 8B:
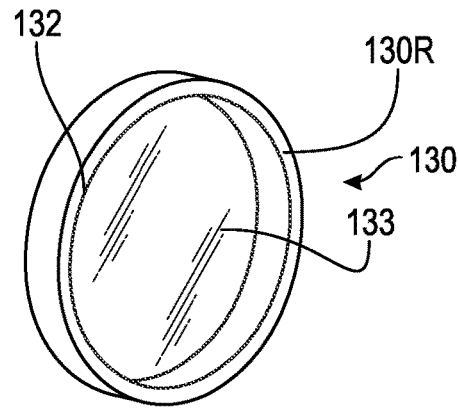
Figure 8C:
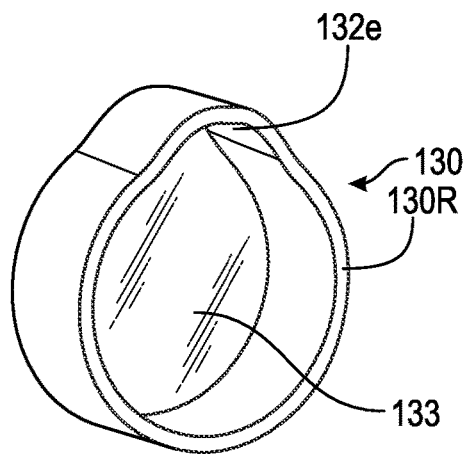
Figure 8D:
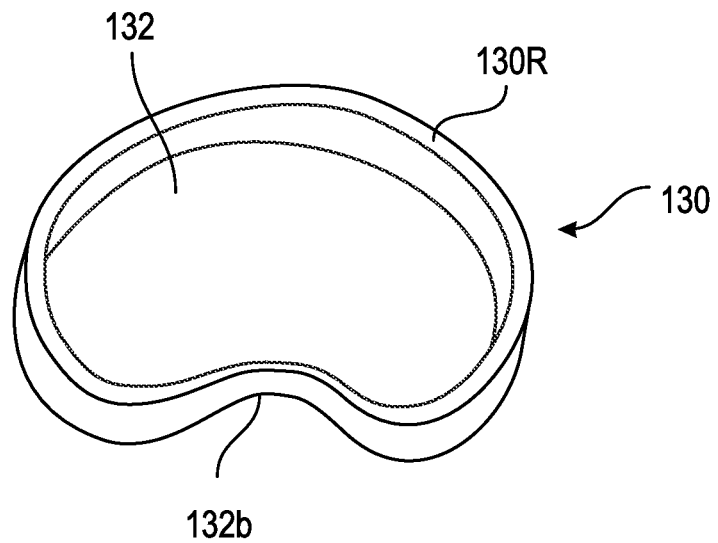
Figure 8E:
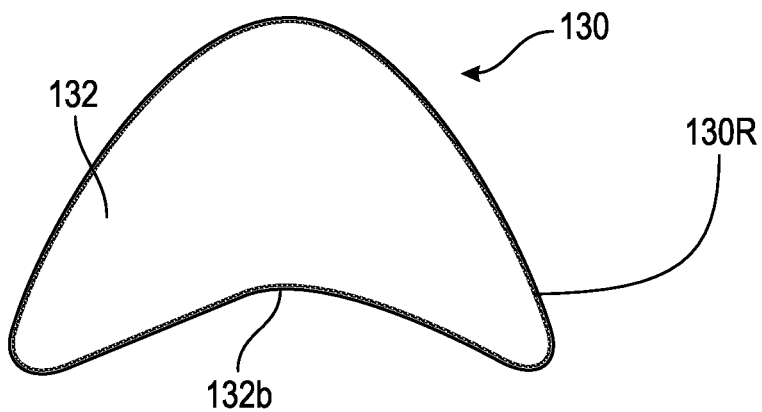

In one or more embodiments, the gripping feature 130 comprises the opening 132 through the film 104. In the embodiment shown in FIGS. 5A-C, the opening 132 is in the shape of a circle. However, the opening 132 shape is not limited to the shape of a circle. FIGS. 8A-8E shows alternate embodiments of non-limiting examples of alternative shapes. In FIGS. 8A and 8C, the opening 132 is in the shape of a circle including an elongate top surface 132e. In FIG. 8B, the opening 132 is circular or in the shape of a circle. In FIGS. 8D and 8E, the opening 132 is in the shape of an oval having a recessed bottom surface 132b, providing an irregularly shaped opening.

In some embodiments, the raised area 130R comprises a reinforcement surrounding the opening 132, the reinforcement comprising a height h that is greater than a thickness of the film 104 surrounding the opening, the reinforcement having a tearing strength that is greater than the tearing strength of the film 104. The tearing strength of the reinforcement according to one or more embodiments is at least 1.5 times, at least 2 times, at least 3 times, at least 4 times, at least 5 times, at least 6 times, at least 7 times, at least 8 times, at least 9 times, at least 10 times or at least 20 times the tearing strength of the film 104. The tearing strength of the reinforcement should provide sufficient strength so that when a user exerts a pulling force on reinforcement, the film 104 tears at the tear-enabling feature 120 so that the first end 101 of the package 110 can be torn at the tear-enabling feature to expose the medical device 190 to be removed from the package 110.

In one or more embodiments, the front side 110F of the enclosure 113 comprises an inside surface 110i in contact with the medical device 190 and an outside surface opposite the inside surface of the front side 110F, and the back side 110B of the enclosure 113 comprises an inside surface in contact with the medical device 190 and an outside surface 110o opposite the inside surface of the back side 110B. In one or more embodiments, the tear-enabling feature 120 comprises both a notch 120n and a perforation 122.

In some embodiments, the notch 120n is u-shaped, and in some embodiments, the notch 120n is v-shaped as shown. In one or more embodiments, the enclosure 113 comprises a flow-wrapped film 104.

Figure 6A:
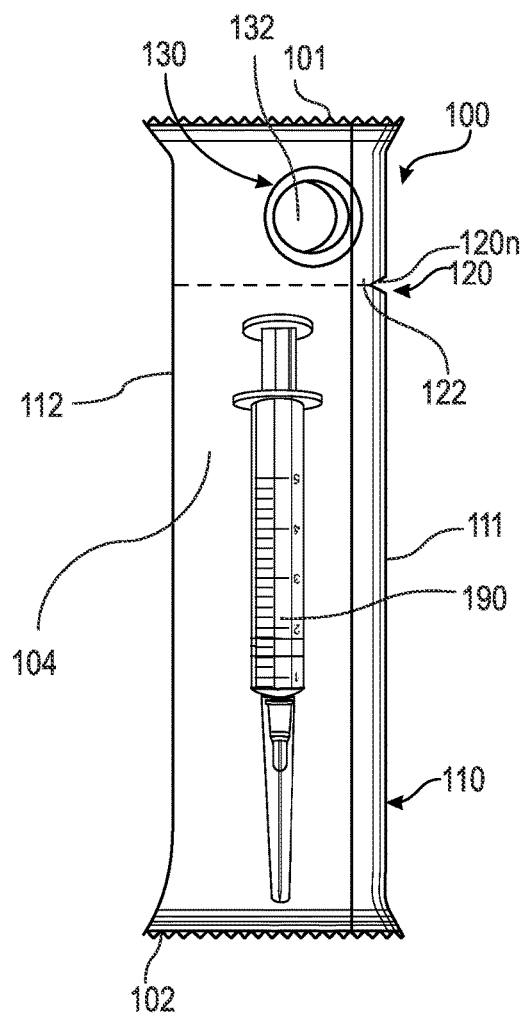
FIG. 6A is a front view of a packaged medical device according to an alternative embodiment of the disclosure.
Figure 6B:
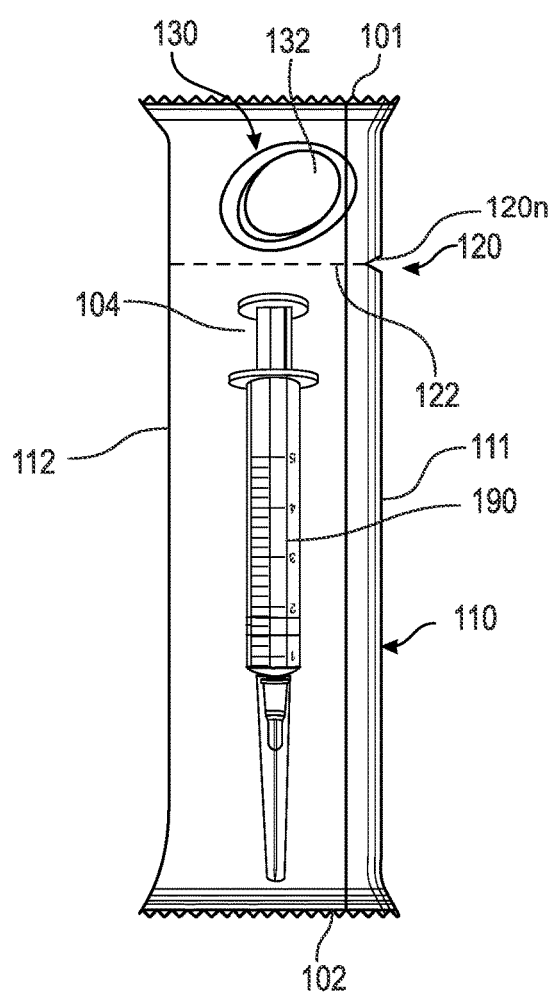
FIG. 6B is a front view of a packaged medical device according to an alternative embodiment of the disclosure.

FIG. 6A shows an alternate embodiment of a packaged medical device 100 comprising a package 110 containing a medical device in which the gripping feature 130 in the form of an opening is not centered between the first edge 11 and the second edge (as shown in FIG. 5A), but instead is positioned closer to the first edge 111. FIG. 6B shows an alternate embodiment of a packaged medical device 100 comprising a package 110 containing a medical device in which the gripping feature 130 in the form of an opening is not centered between the first edge 11 and the second edge (as shown in FIG. 5A), but instead is positioned closer to the first edge 111. In addition, the opening 132 is in the shape of an oval.

Figure 7:
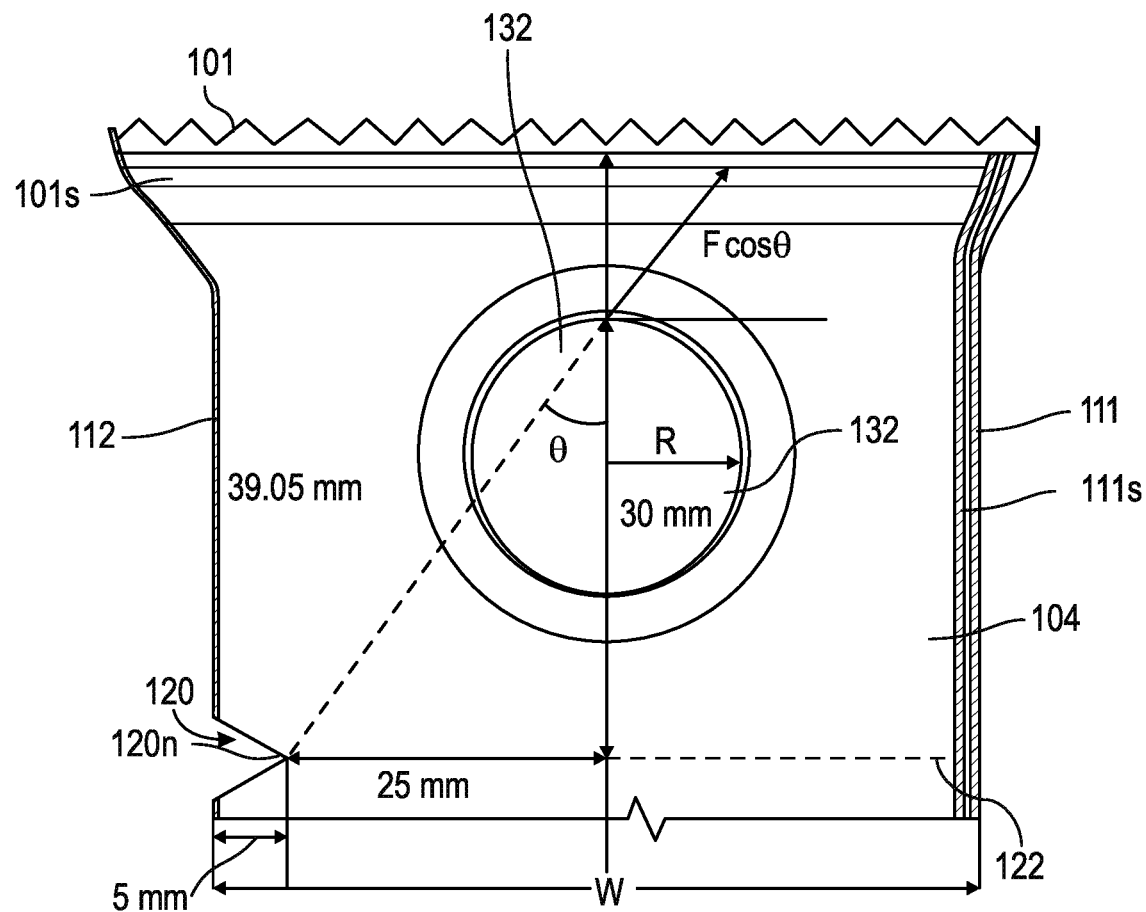
FIG. 7 is a partial front view of the package of FIG. 5A.

Referring now to FIG. 7, in an exemplary embodiment, the opening 132 through the film 104 comprises an internal diameter of 20 mm or greater, or twice the radius R of 10 mm shown in FIG. 7. This opening size permits the opening 132 to be sized so that a finger or a thumb of a user having an average thumb or finger size that can be inserted through the opening 132, or a tool with a hook to be inserted through the opening 132.]. In FIG. 7, the notch has a depth of 5 mm for an overall package width of W of 30 mm. FIG. 7 shows other exemplary dimensions, including an overall package width W of 60 mm (FIG. 7 shows the notch having a width of 5 mm and the distance from the notch edge to the center of 25 mm, and a total package width W would be 2×30 mm). The angle θ is the angle between a line extending from the top of the opening 132 extending to the notch edge and the diameter line of the circle extending vertically from the top of the opening 132. In one or more embodiments, the tear strength at the tear-enabling feature 120 is greater than 0.1 Newtons and less than or equal to 1.3 Newtons. Considering that there are two layers of the film 104, the total tear strength of the package 110 is 2.6 Newtons or less. An average user's thumb can exert a force of 9.7 Newtons when the thumb is extended away from the index finger. The force of the thumb when extending away from the index finger, therefore, acting on the notch V is therefore equal to F cos θ=7.46 Newtons, which is sufficient to tear the package at the tear-enabling feature 120. In one or more embodiments, the notch 102n has a width such that the force to tear open the package is less than 9.7 Newtons.

In one or more embodiments, the packaged medical device 100 comprises stretchable web of material 133 (shown in FIGS. 8B and 8C) attached to the opening 132 through the film 104. The stretchable web of material 133 is configured to permit the user to insert a finger, a thumb or an end of a tool in the opening 132 and restrict the finger, the thumb or the end of the tool from puncturing the stretchable web of material and allowing the user to exert a sufficient tearing force to tear and move the first end 101 of a package 110 away from second end 102 of a package 110 using only one hand. In other words, the stretchable web of material 133 has a puncture resistance and strength the prevents a user's finger or thumb from exiting becoming entangled in the opening, and the stretchable web of material allows the user to exert the tearing force to tear the first end away from the package 110 to expose the medical device 190 and allow the medical device 190 to be removed from the package 110.

Figure 13A:
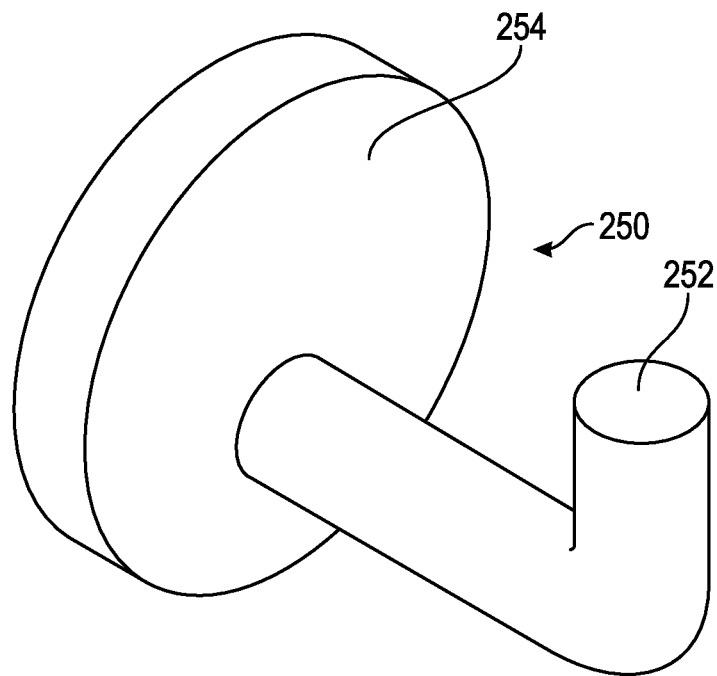
FIGS. 13A and 13B show alternate embodiments of a tool that can be used to open the package according to an embodiment.
Figure 13B:
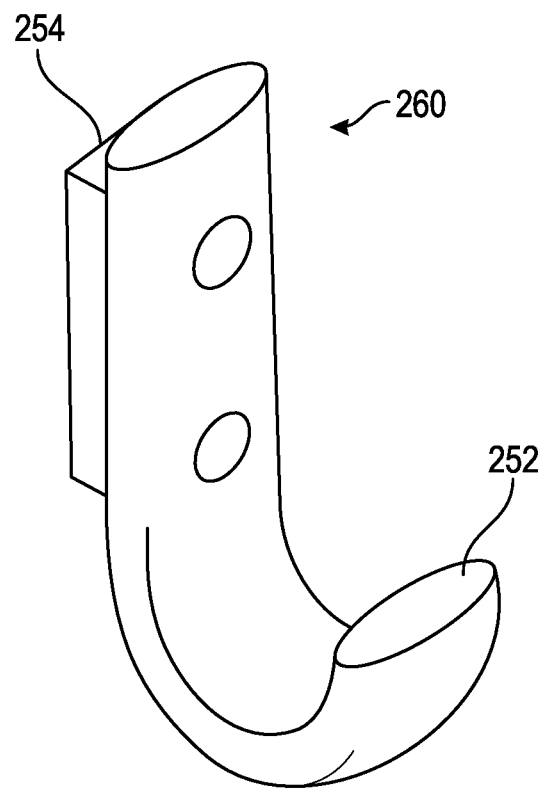

FIGS. 13A and 13B show examples of tools 250 and 260 that can be used to insert into the opening 132 to tear the package 110 open to remove the medical device 190. In FIG. 13A, the tool 25 include a hook 252 and a mount 254 allowing the tool to be mounted to a wall surface of room, or a bed or a wall surface of an ambulance, and the tool can be conveniently placed in a patient treatment area. Similarly, tool 260 include a hook 252 and a mount 254 allowing the tool to be mounted for use. Alternatively, the hook can be placed on an intravenous bag pole. The hook provides leverage when the user grips the package and tears away the top of the package at the tear-enabling feature.

An aspect of the disclosure thus includes a system comprising the packaged medical device 100 described herein and a hook-shaped tool (250 or 260) configured to engage the gripping feature 130.

Figure 14:
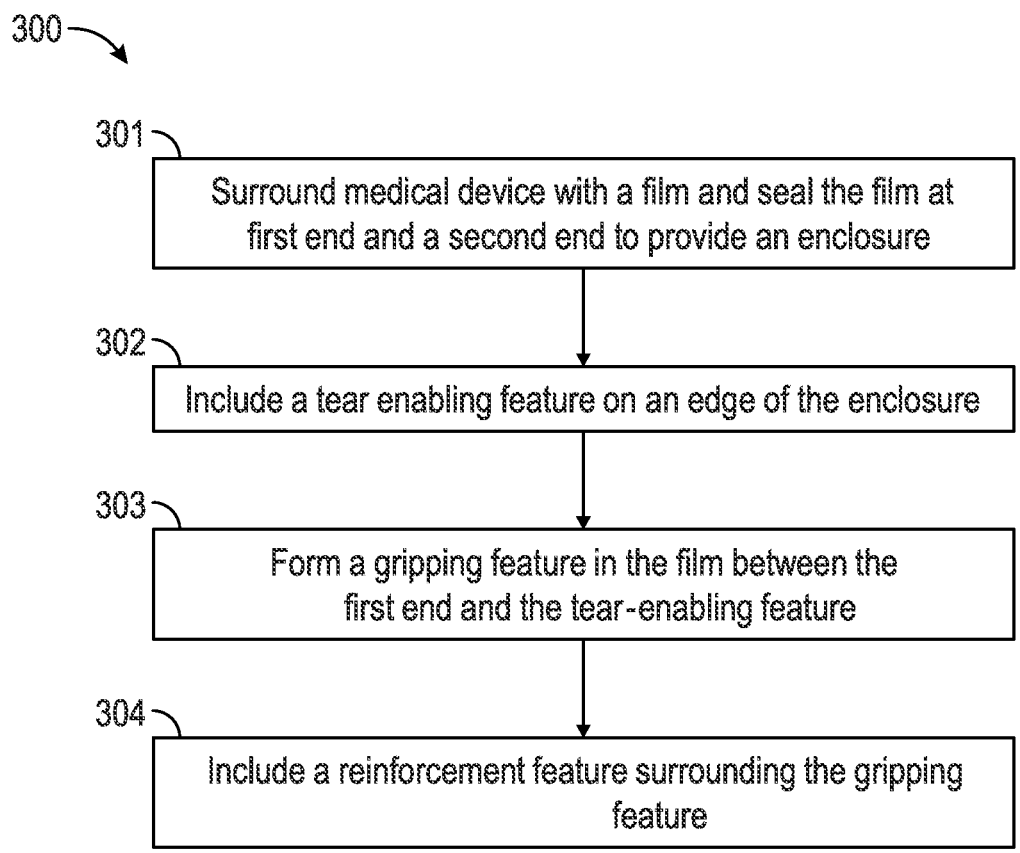
FIG. 14 is a flowchart illustrating a method according to an embodiment.

Referring now to FIG. 14, a method 300 of packaging a medical device 190 in a package 110 comprises at operation 301 surrounding the medical device 190 with a film 104 and sealing the film at a first end 101 and a second end 102 to define an enclosure 113 comprising a front side 110F, a back side 120B, the first end 101, the second end 102, a first edge 111 and a second edge 112, the film 104 comprising a tear strength. At operation 302, the method 300 involves including in the film 104 a tear-enabling feature 120 selected from at least one of a notch 120n and a perforation 122 at a location on one of the first edge 111 and the second edge 112 and adjacent the first end 101, the tear-enabling feature 120 reducing the tear strength of the film at the location of the tear-enabling feature 120. At operation 303 the method includes forming a gripping feature 130 in the film 104 located between the first end 101 and the tear-enabling feature 120, the gripping feature 130 configured to allow a user to use a finger, a thumb or an end of a tool to apply a sufficient tearing force to cause the tear-enabling feature 120 to tear and move the first end 101 of the package 110 away from second end 102 of the package 110 using only one hand and to expose the medical device 190 to be accessed for use. In some embodiments at operation 304, the method includes forming a reinforcement feature surrounding the gripping feature. Thus, in some embodiments of the method 300, the gripping feature 130 comprises at least one of a raised area in the film and an opening through the film, and the method further comprises sealing one of the first edge and the second edge. In some embodiments of the method 300, the gripping feature comprises a raised area in the film, the raised area having a thickness that is greater than a thickness of the film and providing a surface to allow the user to apply the sufficient tearing force. In some embodiments of the method, the gripping feature comprises the opening through the film, the opening extending through the front side and the back side.

In embodiments of the method that comprise including a reinforcement surrounding the opening, the reinforcement comprising a thickness or a height that is greater than a thickness of the film surrounding the opening, the reinforcement having a tearing strength that is greater than the tearing strength of the film. In one or more embodiments, the method includes a flow wrapping process and the enclosure comprises a flow-wrapped film. In some embodiments, the opening in the film 104 has an internal diameter of 20 mm or greater.

Some embodiments of the method include attaching a stretchable web of material to the opening through the film, wherein the stretchable web of material is configured to permit the user to insert the finger, the thumb or the end of the tool in the opening and restrict the finger, the thumb or the end of the tool from puncturing the stretchable web of material and allowing the user to exert a sufficient tearing force to tear and move the first end of the package away from second end of the package using only one hand.

In some embodiments, the film 104 is a flow wrapped film. Flow wrapping, also known as fin-seal wrapping, horizontal bagging, or pillow pouch wrapping, is a quick and economical packaging method. In a flow-wrapping process, the medical device proceeds through a flow wrapping machine, which precisely places a polymer-based packaging film 104 over the medical device and seals the package 110. Flow wrapping incorporates three unique seals consisting of two crimps at the ends (first end 101 has seal 101s and second end 102 has a seal 102s) and a longitudinal fin seal that runs along the back of the package or along one edge (first edge 111 includes seal 111s, however, second edge 112 can have a seal while first edge 111 is not sealed). It will be understood that the unsealed edge, in the embodiment shown second edge 112 is simply folded over and wrapped around the medical device 190.

Flow wrapping machines come in a wide variety of forms, and flow wrapping machines usually include an infeed conveyor belt, a film feed assembly, a forming area, and a discharge area. The medical device is typically placed on an infeed conveyor belt, which transports the product to the forming area. At the forming area, the machine wraps a layer of sealing material around the product, mating the two outside edges of the material at the bottom. The mating edges then pass through a pair of rotating fin seal wheels, which form the longitudinal seal using heat, pressure, or a combination of both. The packaged medical device 109 then moves through a series of rotating cutting heads, or end seal crimpers, which seal the front and back ends of the product while separating the adjoining products into individual packages. After this process, the machine delivers the packaged medical devices to the discharge area, where they accumulate for storage or further packaging.

Flow wrapping operates mainly via horizontal or vertical processes. As their names suggest, vertical flow packing packages medical devices vertically, and horizontal flow packing wraps products horizontally.

In specific embodiments of a manufacturing method, the medical devices 190 such as syringes and the reinforcements are pre-manufactured and come in as raw material inputs for packaging and are placed on the conveyer belt at predefined locations using splits. Laminate rolls come in and are placed on the roller according to a current process. The laminates are placed above and below each unit in a line. Adhesive is put on the laminate section where the reinforcement is located, and the reinforcement is sealed to the film 104. The opening 133 is punched through the film 104. Then each package is cut at predefined length, and the notch is added during an additional notch cutting process. In some embodiments that include the stretchable web of material, the stretchable web of material comprises a thin film of LDPE which is attached on the on the reinforcement using an adhesive or a heat-sealing process. Alternatively, stretchable web of material can comprise any other plastic or rubber that meets the requirements of opening the package and preventing entanglement of the thumb or finger of a user.

Figure 10:
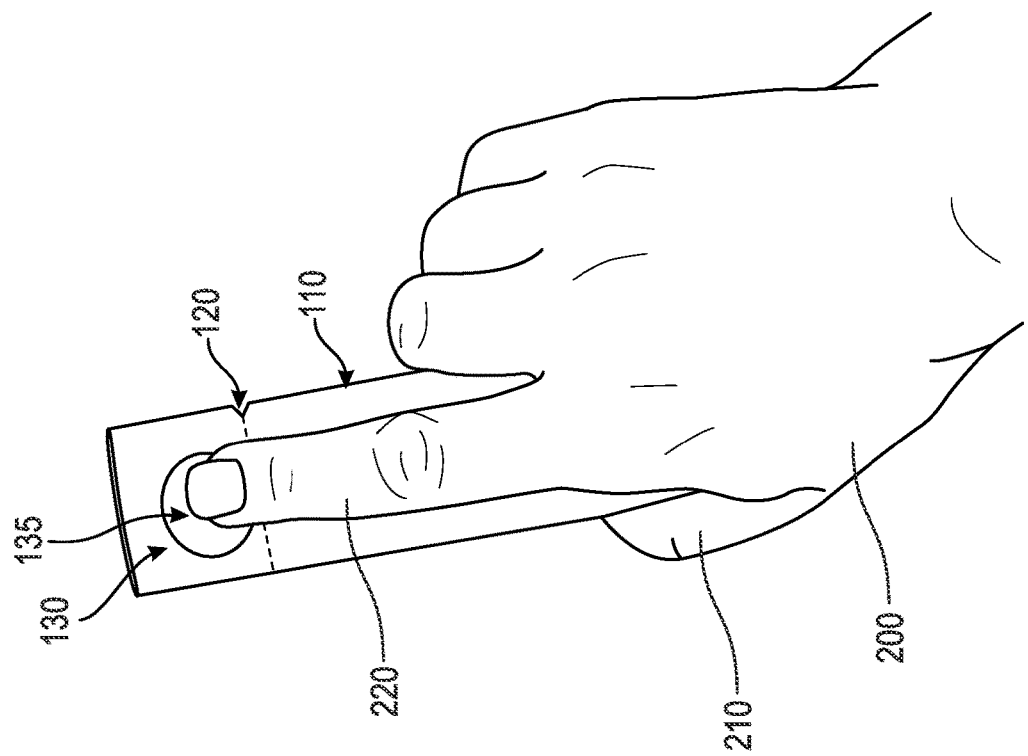
FIG. 10 is a front view showing use of the package according to an embodiment.
Figure 9:
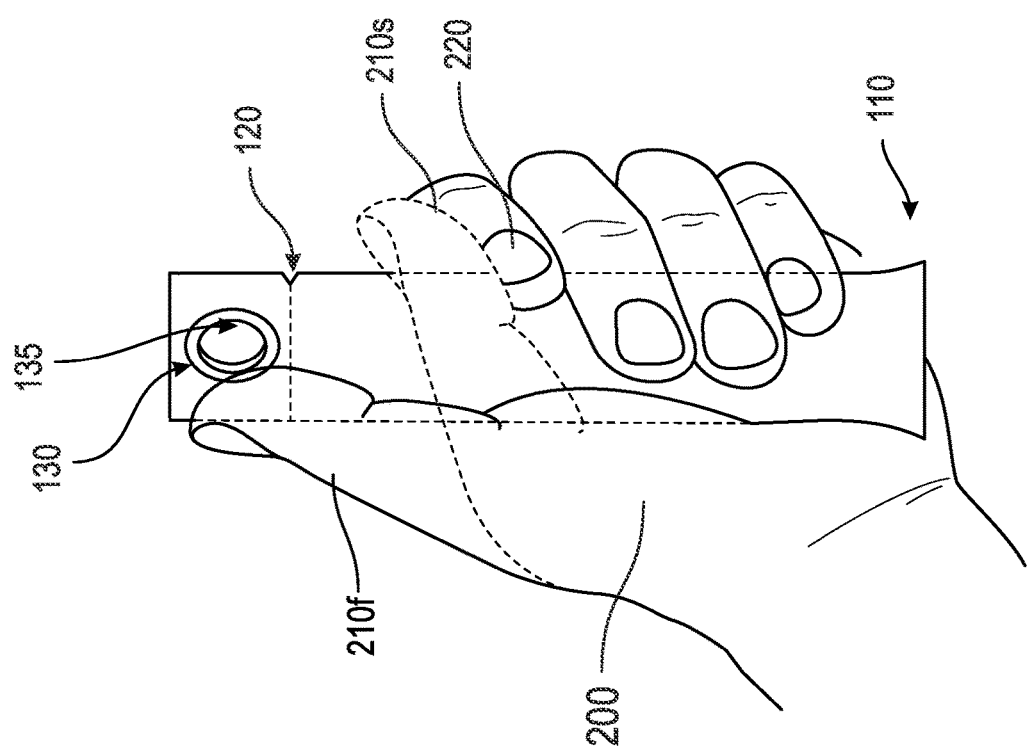
FIG. 9 is a front view showing use of the package according to an embodiment of the disclosure.

FIGS. 9 and 10 show examples of a user using a single hand 200 to open the package 110. In FIG. 9, the user grips the package 110 in the hand, wraps the user's fingers 220 around the package 110 to grip the package 110 firm in the hand 200. Then, at a starting position the user's thumb 210 is shown at 210s, and a user inserts their thumb into the opening 135 and moves the thumb away from the gripped portion of the package with the thumb shown in the finished position 210f. FIG. 10 shows the users gripping the package 110 and placing the index finger 220 in the opening 135 of the package.

Figure 12A:
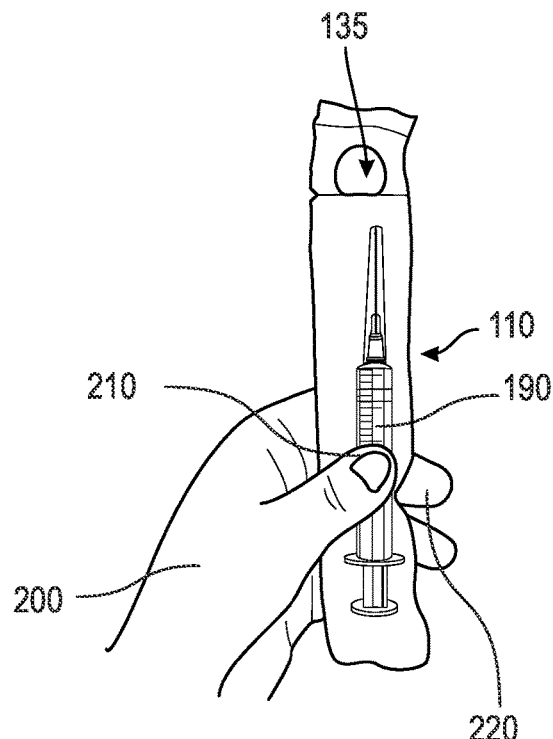
FIGS. 12A-D are front views showing use of the package and illustrating how the package can be opened according to an embodiment.
Figure 12B:
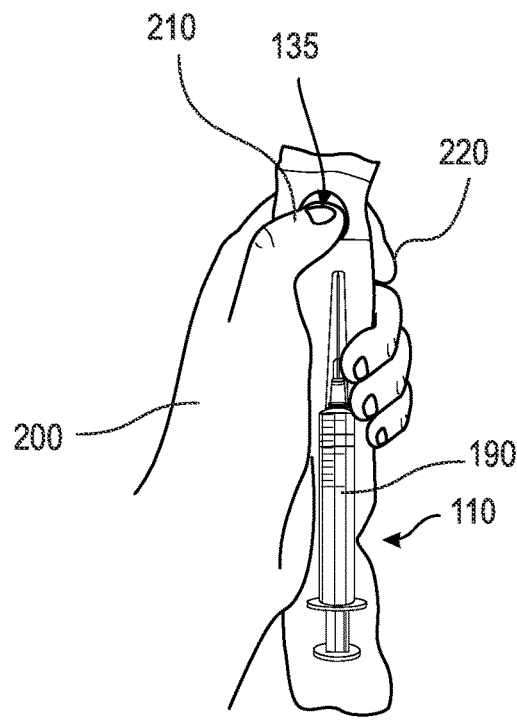
Figure 12C:
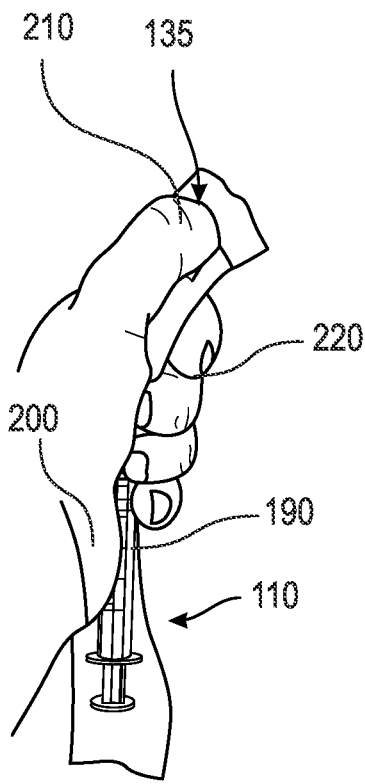
Figure 12D:
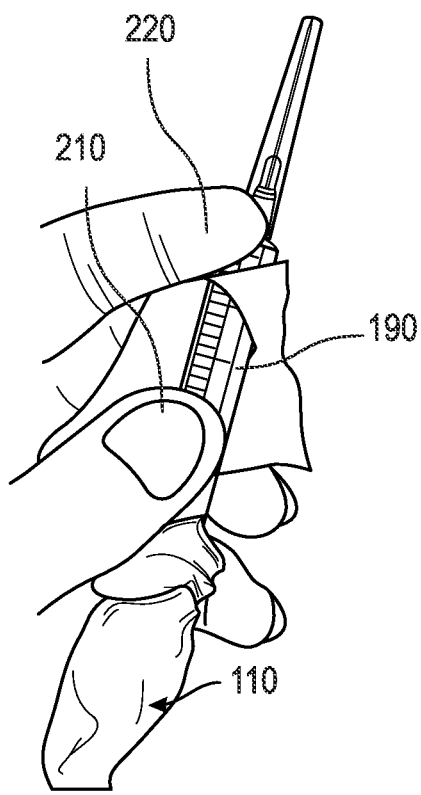

FIGS. 12A-D show another embodiment of a package 110 opening sequence. In FIG. 12A, the user places the package 110 in the user's hand 200, gripping the package 110 enclosing a medical device 190 between the thumb 210 and the fingers 220. In FIG. 12B, the user (e.g., a medical practitioner) inserts a thumb 210 into the opening 135 of the package 110, gripping the package 110 firmly in the user's hand. In FIG. 12, the user exerts an upward force on the opening with the thumb 210 until the top of the package 110 tears away from the remainder of the package. In FIG. 12D, the medical device 190 has been expose and can be removed from the package.

Opening a package 110 with only one hand is less cumbersome for the medical practitioner and enables the medical practitioner to use his/her other available hand for additional tasks. Thus, the present disclosure provides a significant advancement over the current practice of medical device packages. The current practice for opening a pack requires involvement of two hands. This practice presents its own set of challenges during an emergency (e.g., for a paramedic or an emergency medical technician or a nurse), where there can be either a time constraint or space challenges or both. A single hand operation to open package, in this case, provides an easy and a fast access to the product. A package that can be opened with a single hand allows a user such as a medical practitioner to use their other hand to do something else at the same time. In one or more embodiments, the package and the medical device are capable of sterilization and/or sterilized.

Although the disclosure includes a description with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as disclosed.

What is claimed is:

1. A packaged medical device comprising:
    a medical device contained in a package, the package comprising:
    a film surrounding the medical device, the film sealed at a first end and a second end and defining an enclosure comprising a front side, a back side, the first end, the second end, a first edge, and a second edge, the film comprising a tear strength;
    a tear-enabling feature selected from at least one of a notch and a perforation at a location on one of the first edge and the second edge and adjacent the first end, the tear-enabling feature reducing the tear strength of the film at the location of the tear-enabling feature; and
    a gripping feature formed in the film located between the first end and the tear-enabling feature, the gripping feature configured to allow a user to use a finger, a thumb or an end of a tool to apply a sufficient tearing force to cause the tear-enabling feature to tear and move the first end of the package away from second end of the package using only one hand and to expose the medical device to be accessed for use.

2. The packaged medical device of claim 1, wherein the medical device comprises a syringe.

3. The packaged medical device of claim 2, wherein the gripping feature comprises at least one of a raised area in the film and an opening through the film.

4. The packaged medical device of claim 3, wherein the gripping feature comprises a raised area in the film, the raised area having a height that is greater than a thickness of the film and providing a surface to allow the user to apply the sufficient tearing force.

5. The packaged medical device of claim 3, wherein the gripping feature comprises the opening through the film.

6. The packaged medical device of claim 5, wherein the opening comprises a circle shape.

7. The packaged medical device of claim 5, wherein the opening comprises an oval shape.

8. The packaged medical device of claim 5, wherein the opening comprises an irregular shape.

9. The packaged medical device of claim 5, further comprising a reinforcement surrounding the opening, the reinforcement comprising height that is greater than a thickness of the film surrounding the opening, the reinforcement having a tearing strength that is greater than the tearing strength of the film.

10. The packaged medical device of claim 1, wherein the front side of the enclosure comprises an inside surface in contact with the medical device and an outside surface opposite the inside surface of the front side, and the back side of the enclosure comprises an inside surface in contact with the medical device and an outside surface opposite the inside surface of the back side.

11. The packaged medical device of claim 10, wherein the tear-enabling feature comprises both a notch and a perforation.

12. The packaged medical device of claim 11, wherein notch is u-shaped.

13. The packaged medical device of claim 11, wherein the notch is v-shaped.

14. The packaged medical device of claim 2, where in the enclosure comprises a flow-wrapped film.

15. The packaged medical device of claim 5, wherein the opening through the film comprises an internal diameter of 20 mm or greater.

16. The packaged medical device of claim 9, further comprising a stretchable web of material attached to the opening through the film, wherein the stretchable web of material is configured to permit the user to insert the finger, the thumb or the end of the tool in the opening and restrict the finger, the thumb or the end of the tool from puncturing the stretchable web of material and allowing the user to exert a sufficient tearing force to tear and move the first end of the package away from the second end of the package using only one hand.

17. A system comprising:
    the packaged medical device according to claim 1; and
    a hook-shaped tool configured to engage the gripping feature.

18. A method of packaging a medical device, the method comprising:
    surrounding the medical device with a film and sealing the film at a first end and a second end to define an enclosure comprising a front side, a back side, the first end, the second end, a first edge and a second edge, the film comprising a tear strength;
    including in the film a tear-enabling feature selected from at least one of a notch and a perforation at a location on one of the first edge and the second edge and adjacent the first end, the tear-enabling feature reducing the tear strength of the film at the location of the tear-enabling feature; and
    forming a gripping feature in the film located between the first end and the tear-enabling feature, the gripping feature configured to allow a user to use a finger, a thumb or an end of a tool to apply a sufficient tearing force to cause the tear-enabling feature to tear and move the first end of the enclosure away from second end of the enclosure using only one hand and to expose the medical device to be accessed for use.

19. The method of claim 18, wherein the medical device comprises a syringe.

20. The method of claim 19, wherein the gripping feature comprises at least one of a raised area in the film and an opening through the film, and the method further comprises sealing one of the first edge and the second edge.

21. The method of claim 20, wherein the gripping feature comprises a raised area in the film, the raised area having a height that is greater than a thickness of the film and providing a surface to allow the user to apply the sufficient tearing force.

22. The method of claim 21, wherein the gripping feature comprises the opening through the film, the opening extending through the front side and the back side.

23. The method of claim 22, further comprising including a reinforcement surrounding the opening, the reinforcement comprising a height that is greater than a thickness of the film surrounding the opening, the reinforcement having a tearing strength that is greater than the tearing strength of the film.

24. The method of claim 18, wherein the front side of the enclosure comprises an inside surface in contact with the medical device and an outside surface opposite the inside surface of the front side, and the back side of the enclosure comprises an inside surface in contact with the medical device and an outside surface opposite the inside surface of the back side.

25. The method of claim 24, wherein the tear-enabling feature comprises both a notch and a perforation.

26. The method of claim 19, where in the enclosure comprises a flow-wrapped film.

27. The method of claim 23, wherein the opening through the film comprises an internal diameter of 20 mm or greater.

28. The method of claim 27, further comprising attaching a stretchable web of material to the opening through the film, wherein the stretchable web of material is configured to permit the user to insert the finger, the thumb or the end of the tool in the opening and restrict the finger, the thumb or the end of the tool from puncturing the stretchable web of material and allowing the user to exert a sufficient tearing force to tear and move the first end of the enclosure away from the second end of the enclosure using only one hand.

* * * * *